(12) United States Patent
Zimmermann et al.

(10) Patent No.: US 6,583,619 B2
(45) Date of Patent: Jun. 24, 2003

(54) SQUID MICROSCOPE

(75) Inventors: Egon Zimmermann, Inden (DE); Helmut Soltner, Inden (DE); Walter Glaas, Elsdorf (DE); Horst Halling, Pier (DE); Mikkail Faley, Jülich (DE)

(73) Assignee: Forschungszentrum Julich GmbH, Julich (DE)

( * ) Notice: Subject to any disclaimer, the term of this patent is extended or adjusted under 35 U.S.C. 154(b) by 0 days.

(21) Appl. No.: 10/038,166

(22) Filed: Oct. 25, 2001

(65) Prior Publication Data

US 2002/0057085 A1 May 16, 2002

(30) Foreign Application Priority Data

Oct. 26, 2000 (DE) .......................................... 100 53 034

(51) Int. Cl.[7] .............................................. G01R 33/02
(52) U.S. Cl. ....................... 324/248; 505/846
(58) Field of Search ................ 324/248, 235, 324/244, 239; 303/846, 162, 160; 257/31, 32, 34, 36

(56) References Cited

U.S. PATENT DOCUMENTS 5,786,690 A * 7/1998 Kirtley et al. ............... 324/249
6,023,161 A * 2/2000 Dantsker et al. ............ 324/248

OTHER PUBLICATIONS

Design and implementation of a scanning Squid Microscope, L.N.Vu et al. IEEE vol. 3 No. 1 Mar. 1993 4 pages.*
"Design and Implementation of a Scanning Squid Microscope", L.N.VU et al, IEEE transactions on applied superconductivity, vol. 3,No. 1,Mar. 1993, 4 pages.
"High–T Squid Microscope Study of the Effects of microstructur. . .", T.J.Shaw et al, 4 pages.

* cited by examiner

Primary Examiner—Edward Lefkowitz
Assistant Examiner—Subhash Zaveri
(74) Attorney, Agent, or Firm—Herbert Dubno

(57) ABSTRACT

In order to measure magnetic characteristics of a sample, the latter is positioned above the SQUID so that both the SQUID and the sample are supported in a vessel in a gaseous nitrogen space above a liquid nitrogen coolant so that the measurement can take place at ambient pressure and in a nitrogen atmosphere.

14 Claims, 1 Drawing Sheet

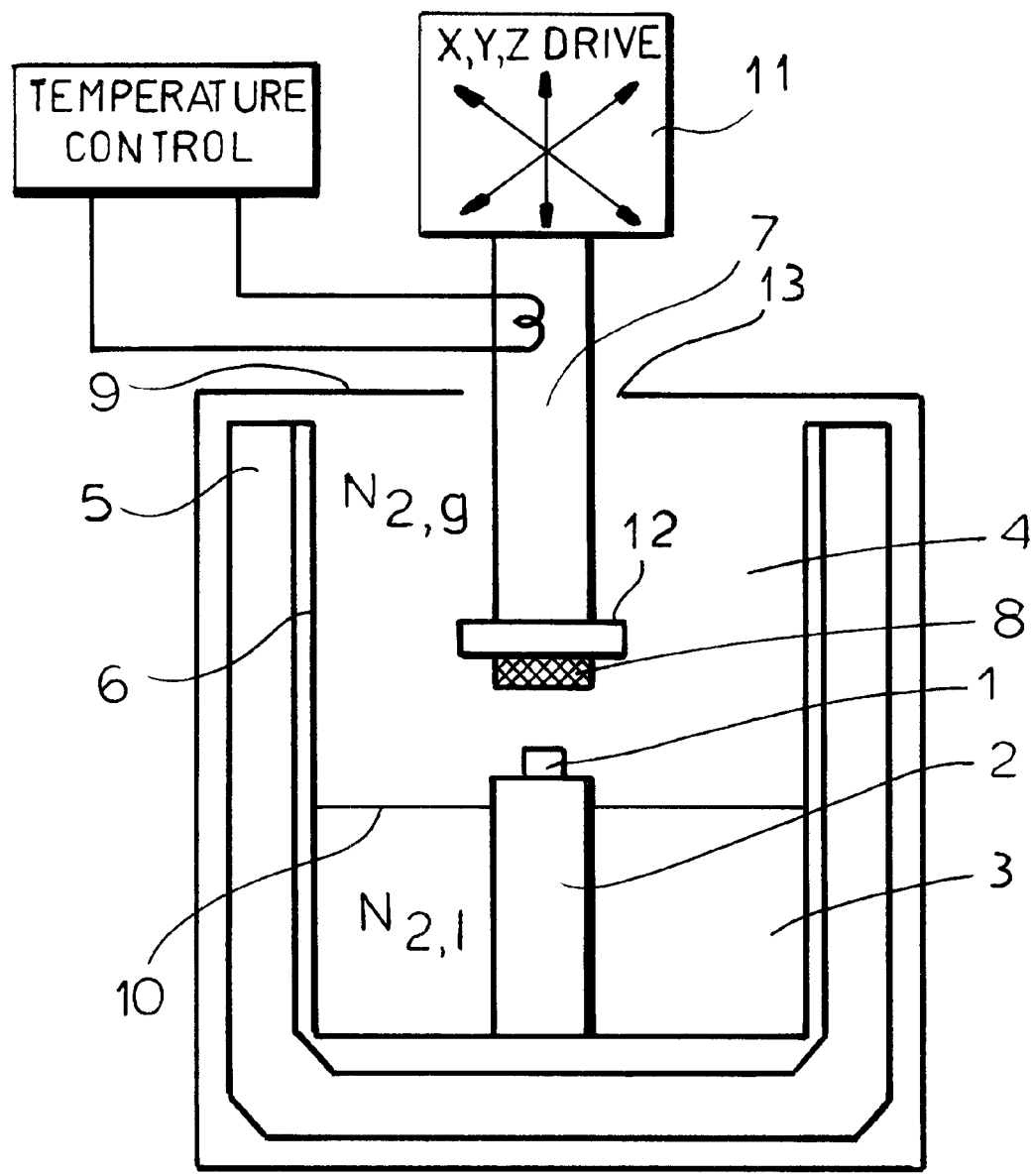

SQUID MICROSCOPE

FIELD OF THE INVENTION

Our present invention relates to a SQUID microscope for measuring or detecting magnetic characteristics of a sample and, more particularly to a method of and to an apparatus for determining magnetic properties of a sample utilizing a SQUID (superconductive quantum interference device).

BACKGROUND OF THE INVENTION

T. J. Shaw et al, "High-$T_c$ SQUID Microscope Study of the Effects of Microstructure and Deformation on the Remanent Magnetization of Steel", IEEE Transactions on Applied Superconductivity, 1999 (9)2, pages 4107 to 4110 describe a SQUID microscope for determining magnetic characteristics of a sample. The SQUID is here mounted on a movable rod and the rod and SQUID are provided in a vacuum chamber which is coupled with a liquid nitrogen supply unit. A sample holder carrying the sample is disposed outside the vacuum chamber and a sapphire window separates the sample and the SQUID.

A drawback of this system is that the sample cannot be placed as close to the SQUID as might be desired. Also, in order to effect the measurement, a vacuum must be generated in the vacuum chamber.

From L. N. Vu et al, "Design and Implementation of a Scanning SQUID Microscope", IEEE Transactions on Applied Superconductivity, Volume 3(1), 1993, pages 1918 to 1921, a SQUID microscope is known. This microscope encompasses a chamber with liquid helium. Connected to this chamber is a sample chamber insulated by an intermediate vacuum layer. In the sample chamber, both the sample and the SQUID are provided, the SQUID being mounted on a movable rod. The rod can be inserted into and withdrawn from the sample chamber and can be sealed toward the exterior via a metallic bellows. The sample and SQUID are cooled by gaseous helium which is in a thermal connection with a liquid helium supply chamber. To cool the microscope, an outer cylinder cooled by liquid nitrogen is additionally provided. The insertion and sealing of the sample in this SQUID microscope is expensive and the need for recirculating gaseous helium is as a rule complex and costly.

OBJECTS OF THE INVENTION

It is the principal object of the present invention to provide an apparatus which is constituted as a SQUID microscope and which by comparison with earlier SQUID microscopes is simple and inexpensive and nevertheless can serve effectively for expelling magnetic properties of a sample.

It is also an object of this invention to provide a method of determining magnetic properties of a sample using a SQUID, whereby drawbacks of prior systems are avoided.

Still another object of the invention is to provide a SQUID microscope and a method of operating same whereby the spacing between the SQUID and the sample can be optionally small.

A further object of the invention is to provide a method of and an apparatus for determining magnetic properties of a sample which enables magnetic property measurement to be carried out at ambient pressure, i.e. without the need to evacuate the space containing the SQUID or sample.

SUMMARY OF THE INVENTION

These objects and others which will become apparent hereinafter are contained, in accordance with the invention in a method of measuring magnetic characteristics of a sample which comprises the steps of:

(a) cooling a SQUID to a superconducting temperature enabling the SQUID to respond to magnetic characteristics of a sample;

(b) juxtaposing the SQUID at superconducting temperature and the sample in a gaseous nitrogen atmosphere at ambient pressure; and (c) effecting a measurement with the SQUID at superconducting temperature of a magnetic property of the sample in the gaseous nitrogen atmosphere at the ambient pressure.

The apparatus of the invention is thus a SQUID microscope which can comprise:

an upwardly open vessel;

a SQUID holder in the vessel configured to cool a SQUID to a superconducting temperature enabling the SQUID to respond to magnetic characteristics of a sample;

a SQUID mounted on the SQUID holder in the vessel and adapted to be cooled to the superconducting temperature enabling the SQUID to respond to magnetic characteristics of the sample; and a sample holder in the vessel carrying a sample juxtaposed with the SQUID in a gaseous nitrogen atmosphere at ambient pressure whereby measurement of a magnetic property of the sample can be effected with the SQUID at superconducting temperature in the gaseous nitrogen atmosphere at the ambient pressure.

The SQUID is preferably cooled in step (a) with liquid nitrogen and the SQUID and sample can thus be provided in an upwardly open vessel containing this liquid nitrogen to a level just below the SQUID so that the SQUID and the sample are both disposed in the gaseous nitrogen atmosphere overlying the liquid level in this vessel. The vessel itself may be a cryostat and the cryostat can be provided with a lining of a $\mu$ metal shield.

The sample and hence the sample holder preferably is located above the SQUID and the SQUID holder can be a sapphire rod which is immersed in the liquid nitrogen.

More particularly, the method of the invention measures magnetic properties of a sample with a SQUID microscope in which the sample and the SQUID are both in a protective gas atmosphere of nitrogen at ambient pressure, i.e. the pressure of the atmosphere surrounding the apparatus and normally approximately atmospheric pressure. The protective gas atmosphere prevents or limits the condensing out or the freezing out, (sublimation) of undesired components on the surface of the sample and/or of the SQUID. Since the method operates at ambient pressure, expensive vacuum technology can be avoided. The sample change as a rule is simple and quick. The protective gas atmosphere can be supplied directly by the coolant both therebelow, the liquid nitrogen evaporating form its surface located preferably just below the SQUID.

The cooling of the SQUID with liquid nitrogen in the bath surrounding the rod on which the SQUID is mounted, greatly simplifies both the generation of the protective gas atmosphere from the coolant and the cooling action.

The use of an upwardly open vessel can communicate with the ambient atmosphere through the opening at the top of this vessel and which contains the liquid nitrogen amounts to a further simplification of the apparatus since it can ensure the ambient pressure for the SQUID and sample.

When the sample is located above the SQUID it can be raised or lowered and brought as close as may be desirable to the SQUID.

The vessel itself can be a Dewar flask or beaker composed of glass, stainless steel or other metals commonly in use with low-temperature systems and GFK.

The $\mu$ metal shield around the SQUID microscope of the invention reduces or eliminates distortion of the magnetic field applied to the SQUID and thus improves the measurement precision. The shield can form the opening communicating between the external atmosphere and the nitrogen blank in the vessel and this opening can be such as to just permit passage of the sample holder.

When the sapphire rod is used as a support for the SQUID, it can simultaneously serve as a heat transfer element between the liquid nitrogen bath and the SQUID. A sapphire rod has good thermal conductivity and very poor electrical conductivity.

The SQUID cooling can be independent from that of the sample and vice versa so that measurements can be taken even when the SQUID and the sample are at different temperatures.

When the gaseous nitrogen develops from the liquid nitrogen bath below the SQUID, it can serve to drive any moisture or air from the vessel and thus permit operation of the apparatus for long periods of time. The fact that moisture is driven out of the system prevents the SQUID, which is located above the liquid nitrogen level in the nitrogen atmosphere from icing up. The evaporated coolant thus forms the protective gas atmosphere.

Since the SQUID and the sample are not separated by a window in the SQUID microscope according to the invention, the sample can be practically brought into contact with the SQUID. A pressure sensor or contact sensor can be provided to output a signal upon contact of the sample with the SQUID and thus allow a process adjustment of the spacing between the SQUID and the sample.

The SQUID microscope of the invention has not only the advantage that it permits investigation of magnetic properties of the samples at ambient pressure, but also that expensive vacuum pumps and like technology can be avoided. Condensation or other deposition of undesired materials on the sample surfaces and/or on the SQUID are precluded and the freezing out of water on the sample surface is especially avoided.

Access to the SQUID or the sample for replacement or checking and even during the measurement (e.g. quality control) is ensured and the apparatus of the invention is especially characterized by permitting quick sample and SQUID replacement.

The distance between the sample and the SQUID can be as small as 1 $\mu$m and, when the SQUID is a HTSL (high temperature superconductor) SQUID, the cooling is relatively simple and the SQUID and sample can be independently cooled or heated.

BRIEF DESCRIPTION OF THE DRAWING

The sole FIGURE of the drawing is a schematic illustration of a SQUID microscope according to the invention.

SPECIFIC DESCRIPTION

The drawing shows schematically a SQUID microscope in which the SQUID 1 is mounted on a sapphire rod 2 which is mostly immersed in a liquid nitrogen bath 3. Because of its high thermal conductivity and its low electrical conductivity, the heat is conducted away from the SQUID 1 so as to maintain it at a temperature of, say, 77 K and can provide sufficient cooling. The SQUID may be a high-temperature superconductor SQUID. The SQUID itself is located above the liquid/gas interface 10 of the nitrogen bath 10.

Because of evaporation of the liquid nitrogen from the bath, there is a gaseous nitrogen atmosphere 4 above the liquid nitrogen 3. This gaseous nitrogen displaces the air and any moisture from the region around the SQUID so that the SQUID 1 which remains for long periods of time above the liquid nitrogen surface 10 without icing up.

The vessel for the nitrogen can be a simple cryostat 5, for example a glass cryostat. The SQUID and its rod 2 are mounted in the vessel in the holder 6.

The sample 8, whose magnetic properties are to be measured, is mounted on a holder 7 which can form part of an x, y, z drive 11 capable of displacing the sample along the x, y and z axes to effect a three-dimensional scanning of the magnetic field around the sample 8 by the SQUID 1.

The holder 7 can be equipped with a measure sensor or contact sensor 12 which can detect contact of the sample 8 with the SQUID 1 and thus, via the control for the drive 11, position the sample 8 at a precise distance above the SQUID 1.

The vessel is provided with a $\mu$ metal shield 9 which prevents magnetic distortion of the field detected by the SQUID. This shield can have a small opening 13 around the holder 7 so that there is only sufficient clearance for movement of this holder and enough space to enable the gas blanket 4 above the liquid nitrogen to communicate with the ambient atmosphere. The $\mu$ metal shield 9 can thus provide optimum shielding of the SQUID 1 juxtaposed with the sample 8.

The measurement of the magnetic field of the sample may be effected by the method described in either of the aforementioned references.

We claim:

1. A method of measuring magnetic characteristics of a sample, comprising the steps of:
    (a) cooling a SQUID to a superconducting temperature enabling said SQUID to respond to magnetic characteristics of said sample;
    (b) juxtaposing said SQUID at said superconducting temperature and the sample in a protective gas atmosphere at ambient pressure in an upwardly open vessel, said protective gas atmosphere preventing deposit of undesirable components on the SQUID or sample; and
    (c) effecting a measurement with said SQUID at superconducting temperature of a magnetic property of said sample in said protective gas atmosphere at said ambient pressure.

2. The method defined in claim 1 which comprises cooling said SQUID in step (a) with liquid nitrogen.

3. The method defined in claim 2 wherein said SQUID and said sample are provided in said upwardly open vessel containing said liquid nitrogen.

4. The method defined in claim 1 wherein said SQUID and said sample are provided in a gaseous nitrogen atmosphere above liquid nitrogen.

5. The method defined in claim 1 wherein said sample is disposed above said SQUID in steps (b) and (c).

6. A SQUID microscope for measuring magnetic characteristics of a sample, comprising:
    an upwardly open vessel;
    a SQUID holder in said vessel configured to cool a SQUID to a superconducting temperature enabling said SQUID to respond to magnetic characteristics of said sample;
    a SQUID mounted on said SQUID holder in said vessel and adapted to be cooled to said superconducting temperature enabling said SQUID to respond to magnetic characteristics of said sample; and a sample holder in said vessel carrying a sample juxtaposing said sample and with said SQUID in a protective gas atmosphere at ambient pressure whereby measurement of a magnetic property of said sample can be effected with said SQUID at said superconducting temperature in said protective gas atmosphere at said ambient pressure, said protective gas atmosphere preventing deposit of undesirable components on said SQUID and said sample.

7. The SQUID microscope defined in claim 6 wherein said sample holder is located above said SQUID.

8. The SQUID microscope defined in claim 7 wherein said vessel contains a cooling medium.

9. The SQUID microscope defined in claim 8 wherein said cooling medium is liquid nitrogen.

10. The SQUID microscope defined in claim 9 wherein said vessel contains a bath of liquid nitrogen below the gaseous nitrogen.

11. The SQUID microscope defined in claim 10 wherein said liquid nitrogen has a level below said SQUID.

12. The SQUID microscope defined in claim 6, further comprising a shield of $\mu$-metal surrounding said SQUID and said sample.

13. The SQUID microscope defined in claim 6, wherein said SQUID holder is a sapphire rod.

14. The SQUID microscope defined in claim 6, further comprising a temperature controller for said sample independent of a temperature of said SQUID.

* * * * *